United States Patent [19]

Brenner et al.

[11] Patent Number: 4,973,320
[45] Date of Patent: Nov. 27, 1990

[54] TISSUE-COMPATIBLE MEDICAL DEVICE AND METHOD FOR MANUFACTURING THE SAME

[75] Inventors: Otto Brenner, Edingen; Wolfgang Ermert, Weinheim; Helmut Eschwey, Gorxheimertal; Gerd Esswein, Maxdorf; Günter Schuhmacher, Weinheim, all of Fed. Rep. of Germany

[73] Assignee: Firma Carl Freudenberg, Weinheim, Fed. Rep. of Germany

[21] Appl. No.: 227,374

[22] Filed: Aug. 2, 1988

[30] Foreign Application Priority Data

Aug. 4, 1987 [DE] Fed. Rep. of Germany ....... 3725728

[51] Int. Cl.$^5$ ............................................. A61M 5/325
[52] U.S. Cl. .................................................... 604/265
[58] Field of Search ........................ 604/265; 523/107; 525/440

[56] References Cited

U.S. PATENT DOCUMENTS

| 3,279,996 | 10/1966 | Long, Jr. et al. | |
|---|---|---|---|
| 3,562,352 | 2/1971 | Nyilas | 525/440 |
| 4,603,152 | 7/1986 | Lavrin et al. | 604/265 |
| 4,612,337 | 9/1986 | Fox, Jr. et al. | 523/113 |
| 4,867,968 | 9/1989 | Allen | 604/96 |

FOREIGN PATENT DOCUMENTS 0068385  9/1986  European Pat. Off. .

*Primary Examiner*—Stephen C. Pellegrino
*Assistant Examiner*—Sharon Rose
*Attorney, Agent, or Firm*—Kenyon & Kenyon

[57] ABSTRACT

A medical device which can be introduced into the body tissue of a human or animal comprises a matrix of a polyurethane elastomer with organic silicone polymer units built into the main polymer chain and an oligodynamic agent spatially distributed uniformly within the matrix. The oligodynamic agent releases bacteriocidal or microbicidal metal ions when exposed to body tissues. The method for manufacturing the medical device is characterized by the addition of the oligodynamic agent in a solid or dissolved form prior to the reaction of the educts with isocyanate.

9 Claims, No Drawings

TISSUE-COMPATIBLE MEDICAL DEVICE AND METHOD FOR MANUFACTURING THE SAME

FIELD OF THE INVENTION

The present invention relates to tissue compatible medical devices which can be introduced into body tissue, such as catheters, prostheses and the like which include metal ions having antimicrobial activity, and a method for making the same.

BACKGROUND OF THE INVENTION

It is well known in the medical arts that the use of medical devices such as catheters and the like which penetrate and remain in contact with living tissues is problematic because of infections caused by microbial growth which occurs at the interfaces of these devices with the tissues over extended periods of time.

The antibacterial activity of heavy metal ions such as gold, silver or copper is well known. These heavy metal ions are often referred to as being "oligodynamic" (for instance, this term is utilized to describe the antimicrobial activity of heavy metal ions in The Journal of Urology, Vol. 121, January 1979, page 40). Oligodynamic agents are especially noted for their ability to provide an antibacterial effect in small quantities. These agents are utilized in medical technology for equipping plastic endoprostheses or hose-shaped catheters and the like, such as urine tube catheters, in order to provide the same with antimicrobial activity for extended periods of time.

For instance, U.S. Pat. No. 4,054,139 (Crossley) discloses the application of at least one oligodynamic agent on both the exterior and interior surfaces of tube-like catheters. By "exterior surface" it is meant that surface which comes in contact with body tissues, while "interior surface" denotes that portion of the device through which fluids may flow in or out of the body. The oligodynamic agent is present in thin layers of about 0.001 inch thickness or less of a solid coating formed by 10% by weight micron-sized particles of the agent in an essentially immobile, highly viscous suspension of human albumin. The coating may be placed on a proteinaceous matrix or a matrix formed from organic plastics such as polyethylene, polyvinyl-chloride, and polytetrafluoroethylene.

U.S. Pat. No. 4,612,337 (Fox, Jr. et al.) discloses a method for making the surface of such a medical device more absorbent for oligodynamic agents by soaking the polymeric material of the device with a solution of an oligodynamic agent dissolved in an organic solvent such as ethanol, soaking the polymeric material with an organic solvent for a metal salt, and thereafter resoaking the polymeric material in the solution of oligodynamic agent in organic solvent. The polymeric material is dried after each soaking step, the last time after washing. Suitable polymeric materials were said to include polyamide, polyester, polyethylene, polypropylene, polystyrene, polytetrafluoroethylene, polyurethane, polyvinylchloride, cellulose acetate, silicone elastomers, collagen, and silk. The intermediate soaking step is said to appreciably increase the incorporation of the oligodynamic agent into the polymeric material.

While the increased incorporation of the oligodynamic agent has been found to be advantageous, the process according to the afore-mentioned Fox, Jr. et al. patent is unsatisfactory because it is time, labor and cost intensive, especially when it is desired to equip the medical device with antimicrobial action on both the interior and exterior surfaces.

Furthermore, since the oligodynamic agents which are present are only bound in the surface zones of the polymer material, their availability is limited as to time and due to their brief residence on the surface. During long-term treatment this translates into a frequent, painful and risky exchange with newly coated devices.

Another problem arises when the devices to be used intracorporally have a spatial form which is not "two-dimensional", i.e., catheters and prostheses. The ability to embed such devices with oligodynamic agents is limited by slightly larger material thicknesses. In the case of silicone elastomers, the ability to embed oligodynamic agents to any appreciable depth from the surface is limited because the inner areas of this material are not sufficiently accessible to body fluids to promote the release of metal ions (due to the hydrophobic properties of the silicone elastomer itself). Therefore, even if these substances are embedded more deeply into the silicone elastomer, there is no available carrier means by which they can migrate to the surface in order to display their antimicrobial activity in the body tissue surrounding the catheter.

Alternatively, the use of materials which are sufficiently hydrophilic (such as polyurethane) to allow the exposure of deeply embedded oligodynamic to body fluids would appear to allow the reversible embedment of these substances down to their innermost zones. However, it has been found that devices with such a design have, as measurements have shown, such low delivery rates for oligodynamically active substances that a sufficient quantity of active metal ions, as measured by the concentration of the germs to be destroyed, is not available for long-term application.

Finally, European Pat. No. 0 068 385, discloses the pronounced antithrombogenic action of an elastomer comprising a polyurethane or a polyurethane urea containing an organic silicon polymer in the main chain and the advantageous use of the same for medical formed parts which are brought into direct contact with blood. Therein, block copolymers known from U.S. Pat. No. 3,562,352 (Nyilas) of a polyurethane and an organic silicone polymer with less silicone than polyurethane units are discussed with respect to their mechanical and antithrombogenic properties upon direct contact with blood and a novel advantageous variant is described wherein 1 to 50%, and preferably 4 to 15% by weight of an organic silicone polymer with a molecular weight of 500 to 10,000 and softening polyether or polyester segments are introduced into the polymer main chain. However, European Pat. No. 0 068 385 is limited to its discussion of the antithrombogenic activity of the elastomer. There is no suggestion therein to coat or embed any type of medicinally active agents, and more specifically antimicrobial agents, onto the surface of this elastomer or otherwise.

It is an object of the present invention to provide a medical device which can be used on or in the living body and can penetrate body tissues which exhibits a substantially increased delivery capacity for antimicrobial (oligodynamic) agents which give off metal ions and which has good tissue compatibility.

It is another object o the present invention to provide a medical device which is capable of releasing oligodynamic agents in controlled amounts over an extended period of time to both its interior and exterior surfaces when it comes into contact with body fluid, etc.

It is a further object of the present invention to provide a method for manufacturing a medical device in which a spatially uniform embedment of the oligodynamic agent into the polymeric matrix is made possible without the necessity of elaborate mechanical or chemical after-treatment of the material or the finished part.

SUMMARY OF THE INVENTION

In accordance with the above-mentioned objectives, the present invention relates to a tissue compatible medical device for intracorporeal insertion comprising a matrix comprising a polyurethane elastomer having a main chain which includes less than about 50% by weight of an organic silicone polymer with a molecular weight of from about 500 to about 10,000, and an oligodynamic agent embedded in a spatially uniform distribution within said matrix which releases metal ions when exposed to body fluids. The oligodynamic agent comprises from about 1 to about 15% by weight of the total weight of the matrix.

Optionally, the polyurethane elastomer includes a plurality of softening polyether or polyester segments, or the block copolymers thereof.

In further embodiments of the present invention, the matrix also includes chain extenders and/or cross-linking agents as additives to impart thermosetting properties to the medical device.

Preferably, the oligodynamic agent comprises the salts, oxides, carbides, and/or organometallic compounds of certain well known heavy metals such as gold, silver, copper, cerium, zinc and the like, or mixtures thereof. Examples of preferred oligodynamic agents include silver nitrate, zinc nitrate, cerium chloride and the like. In addition, it is also preferred that these substances have a particle size not greater than 50 microns.

The present invention also relates to a method for manufacturing a tissue-compatible medical device which gives off microbicidal metal ions upon contacting body fluids, comprising mixing a polyol with an organic silicone polymer having a molecular weight from about 500 to about 10,000, and admixing an oligodynamically active substance capable of giving off microbicidal metal ions and having a particle size of less than about 50 microns with said silicone polyurethane elastomer to produce a prepolymer. The prepolymer is then reacted with a suitable amount of an organic isocyanate, and the mixture is dehydrated to produce a polyurethane elastomer comprising from about 1 to about 15% by weight of said oligodynamic agent. The resulting polyurethane elastomer material is then shaped into the desired form.

In another embodiment of the method of present invention, the oligodynamic agent is highly water soluble and is admixed as an aqueous solution before the isocyanate is added. The solids content of the aqueous solution is from about 1 to 15% by weight of the polyurethane elastomer.

DETAILED DESCRIPTION

The class of materials used to form the polyurethane elastomeric matrix of the present invention, which as previously related are known per se, are referred to as "silicone polyurethanes" for the purposes of the present invention.

The preparation and properties of such materials are not critical for the present invention and can be derived from the state of the art, depending on the desired requirements without inventive activity within the scope of the teachings herein. In particular, the preparation and properties of such materials are set forth in previously mentioned U.S. Pat. No. 3,562,352 (Nyilas) and European Pat. No. 0 068 385, both of which are hereby incorporated by reference.

The polyol compounds used in the manufacture of the polyurethane elastomers of the present invention may comprise any compound of the type used for reaction with isocyanate to form polyurethanes. Included in this category are diol compounds such as polyethers, polyesters and polycaprolactones.

The organic silicone polymer compounds used in the present invention are preferably polysiloxanes such as polydimethylsiloxane, methylphenylsiloxane, fluoroalkylmethylpolysiloxane and the like.

Further, it is possible to use any isocyanate compound of the type used for the manufacture of polyurethane, although diisocyanates are particularly preferred.

The medical device of the present invention can penetrate living body tissues due to its excellent tissue compatability while providing a substantially increased delivery capacity for oligodynamic agents which release metal ions when exposed to body tissues.

The spatially uniform embedment of 1 to 15 wt. % of these oligodynamic agents according to the invention in the silicone polyurethane matrix increases the usable amount of the available ions over the customary coatings by 40% or more.

Because of the matrix utilized herein and the unique nature in which it is formed, the medical devices of the present invention are capable of releasing these metal ions in controlled amounts over an extended period of time to each of its exposed surfaces when in contact with body fluids and the like.

It has surprisingly been found that contact of body fluid with the inner regions of the silicone polyurethane material, which had heretofore been known as advantageous only for other purposes, is reliably ensured if the polymer matrix has thicknesses of up to the 2mm customary for devices of this type.

The medical device of the present invention contact with the body tissue including for example, endoprostheses, catheters, probes, endoscopes, implants, drainage tubes and the like.

Since the polymer matrix of silicone polyurethane forming the device contains the oligodynamic agent in its entirety according to the invention there is, besides the advantage of dispensing the metal ions toward both exposed surfaces of the device body, the further advantageous effect that toward the start of the application, when an increased number of bacteria, microbes and germs may be present, an increased quantity of oligodynamic agent is given off as soon as the superficial regions of the matrix have been saturated with body fluid. After an extended dwell time, a steady decrease in the supply of metal ions occurs because their release will be largely influenced by the path length of the metal ions in the migration from the interior of the matrix to its surface.

However, it must be noted that although there is a decrease in supply of metal ions over time, there are enough metal ions present that the small number of potentially newly-arrived germs is killed off immediately. The medical device according to the present invention thereby adapts the delivery rate of metal ions automatically to the quantity of the organisms to be battled at any one time.

In tubular urine catheters designed according to the invention, the additional advantageous effect was observed that encrustations at the catheter, i.e., mineral deposits took place at a distinctly reduced rate or not at all.

In a preferred method of manufacturing the device according to the invention, the polyol, the organic silicone polymer, the isocyanate and optionally the chain extenders and/or the cross-linking agents are reacted with each other and are then brought into the desired form. The oligodynamic agent is admixed as a powder with a particle size of not greater than about 50 microns in a sufficient amount to comprise from about 1 to 15% by weight of the final product, before the isocyanate is added, and is dehydrated together with the polyol. This processing sequence and the fine-grain nature of the active substance allow the separate operations of drying the oligodynamic agent as well as of the polyol and/or the polyol mixture to be combined in a single process step. In addition, the fineness of the particle size of the oligodynamic agent guarantees the possibility of introducing the active substance substantially uniformly over the entire cross-section of the polymer matrix. In this regard, it has been found that if the oligodynamic agent substantially exceed a particle size of 50 microns, a negative effect is possible on the mechanical stability of the matrix.

Another especially preferred method comprises of using a highly water-soluble, metal-ion-dispensing substance instead of the aforementioned powder and by admixing the same as an aqueous solution with a share of solids equivalent to that attained with the addition of powder described above and at the same point as above, followed by subsequent dehydration and then adding the isocyanate. This embodiment has the advantage of being able to introduce the active substance into the matrix in the smallest possible form, namely, as discrete ions (and thereby in an optimal uniform manner). The subsequent dehydration does not lead to larger crystal agglomerates since the polymer matrix permits only the generation of small crystals (not greater than 50 microns). Advantageously, silver nitrate is used in this instance as the oligodynamic agent.

The methods according to the invention have further advantages such as the elimination of all afterwork previously needed to produce such medical devices. Thus, the handling of solvents, swelling or incipient dissolution of the substrate or problems regarding the adhesion of coatings can be circumvented completely.

If a thermoplastic material is to be obtained, the finished polyurethane equipped with active substance is granulated, dried and subsequently either injection-molded or extruded For the manufacture of thermosetting devices such as probes, the shaping is accomplished immediately after the reaction of the starting materials by pouring them into a die.

In any event, the desired medical device can be manufactured in one continuous process step.

DETAILED DESCRIPTION OF THE PREFERRED EMBODIMENTS

The following example illustrates various aspects of the invention. It is not to be construed to limit the claims in any manner whatsoever.

EXAMPLE 1

100 parts of an OH-terminated bifunctional polyester with a molecular weight of 2,000 g/mol (base, adipinic acid, neopentylglykol plus hexanediol), available commercially under the designation Desmophene 2228 (Bayer AG), are mixed with 20 parts of a linear polydimethylsiloxane (molecular weight 2,000 g/mol) in end position and 6 parts of pulverized silver nitrate (grain size $\leq 50$ microns). The mixture is dehydrated for one hour at 120° C. in a vacuum. Thereafter, the prepolymer produced is mixed with 40 parts diphenylmethane-4, 4' diisocyanate and the polymer chain is extended, after completing the reaction, with 9 parts butane diol.

The finished product is allowed to harden on a heating plate, and is subsequently granulated and dried for two hours at 110° C. in a hot-air oven. Finally, the granulate is brought into the form of a urine tube catheter in an injection molding machine.

The catheter fabricated in this manner has the following material properties:

| | |
|---|---|
| Tensile strength (DIN 53 504) | 20 MPa |
| Fracture elongation (DIN 53 504) | 500% |
| Hardness (DIN 53 305) | 70 Shore A |

This data shows the mechanical suitability of the thermoplastic material for the manufacture of catheters and implants.

The following table shows qualitatively and quantitatively the antimicrobial action as well as the capability to deliver oligodynamically acting silver ions for a polyurethane matrix according to the state of the art as compared to a silicone polyurethane matrix according to the present invention.

| | Matrix with $Ag^+$ | |
|---|---|---|
| Test | Polyurethane (Prior Art) | Silicone polyurethane (As in Example: Invention) |
| $Ag^+$ diffusion (mg/l >*) | 0.57 | 0.89 |
| Microbiological Plate diffusion after** | | |
| 2 days | ++++ | ++++ |
| 4 days | ++++ | ++++ |
| 8 days | ++ | ++++ |
| 16 days | + | ++++ |
| 32 days | no inhibition area | ++++ |

*Determination of the silver ion concentration in synthetic urine by means of atom absorption spectral analysis.
**Qualitative observation of the respective inhibition area diameter in the feeding medium with pathogenic germs (Klebsiella oxytoca ATCC 33496; streptococcus faecalis ATCC 29200; enterobacter cloacae ATCC 29006 and staphylococcus epidermidis), referred to the maximum inhibition area diameter (++++).

We claim:

1. A tissue compatible medical device for use on or within a human or animal body, comprising
    a matrix comprising a polyurethane elastomer having a main chain which includes an effective amount of less than about 50% by weight of an organic silicone polymer having a molecular weight of from about 500 to about 10,000, and
    an oligodynamic agent embedded in a substantially spatially uniform distribution within said matrix, said oligodynamic agent comprising from about 1 to about 15% by weight of the total weight of said matrix and releasing metal ions when exposed to body fluids.

2. The device according to claim 1, wherein said polyurethane elastomer further comprises a plurality of softening polyether or polyester segments.

3. The device according to claim 2, wherein said matrix further comprises an effective amount of chain extenders.

4. The device according to claim 3, wherein said matrix further comprises cross-linking agents for imparting thermosetting properties to said device.

5. The device according to claim 1, wherein said oligodynamic agent comprises the salts, oxides, carbides or organometallic compounds of gold, silver, copper or mixtures thereof.

6. The device according to claim 1, wherein said oligodynamic agent is selected from the group consisting of gold, silver, copper and mixtures thereof.

7. The device according to claim 1, wherein said oligodynamic agent comprises silver nitrate.

8. The device according to claim 1, wherein said oligodynamic agent has a particle size not greater than 50 microns.

9. The device according to claim 1, wherein said matrix has a thickness not greater than 2mm.

* * * * *